United States Patent [19]
Mezrich

[11] 4,131,022
[45] Dec. 26, 1978

[54] PULSE-ECHO ULTRASONIC-IMAGING DISPLAY SYSTEM

[75] Inventor: Reuben S. Mezrich, Rocky Hill, N.J.

[73] Assignee: RCA Corporation, New York, N.Y.

[21] Appl. No.: 766,527

[22] Filed: Feb. 7, 1977

[30] Foreign Application Priority Data

Mar. 4, 1976 [GB] United Kingdom ............... 08661/76
Jul. 16, 1976 [GB] United Kingdom ............... 29763/76
Jul. 16, 1976 [GB] United Kingdom ............... 29764/76
Jul. 16, 1976 [GB] United Kingdom ............... 29765/76

[51] Int. Cl.² ........................................... G01N 29/00
[52] U.S. Cl. ...................................... 73/606; 73/625; 73/629; 128/2 V
[58] Field of Search ............... 73/67.5 R, 67.7, 67.8 R, 73/67.8 S, 67.9, 71.5 US, 606, 607, 629, 614, 632, 625, 642, 641, 626; 340/5 MP, 5 H, 8 FT; 128/2 V, 2.05 Z

[56] References Cited

U.S. PATENT DOCUMENTS

| | | | |
|---|---|---|---|
| 2,833,999 | 5/1958 | Howry | 73/642 |
| 3,792,423 | 2/1974 | Becker | 340/5 MP |
| 3,886,490 | 5/1975 | Green | 340/5 MP |
| 3,895,525 | 7/1975 | Eichelberger | 340/5 MP |
| 3,918,024 | 11/1975 | Macovski | 340/5 MP |
| 3,918,297 | 11/1975 | Rocha | 73/607 |
| 3,937,066 | 2/1976 | Green | 340/5 MP |
| 4,016,750 | 4/1977 | Green | 73/629 |

*Primary Examiner*—Stephen A. Kreitman
*Attorney, Agent, or Firm*—H. Christoffersen; Samuel Cohen; George J. Seligsohn

[57] ABSTRACT

An improvement to a pulse-echo ultrasonic-imaging system, which permits the displaying of a three-dimensional representation of internal structure such as the soft tissue within the body of a living human being. The improved system includes a focusing device, such as an acoustic lens or an acoustic axicon, which provides a depth of field for the scanning focused beam which is several times the focused spot size of the scanning focused beam and which is at least as great as the depth dimension of the structure.

11 Claims, 8 Drawing Figures

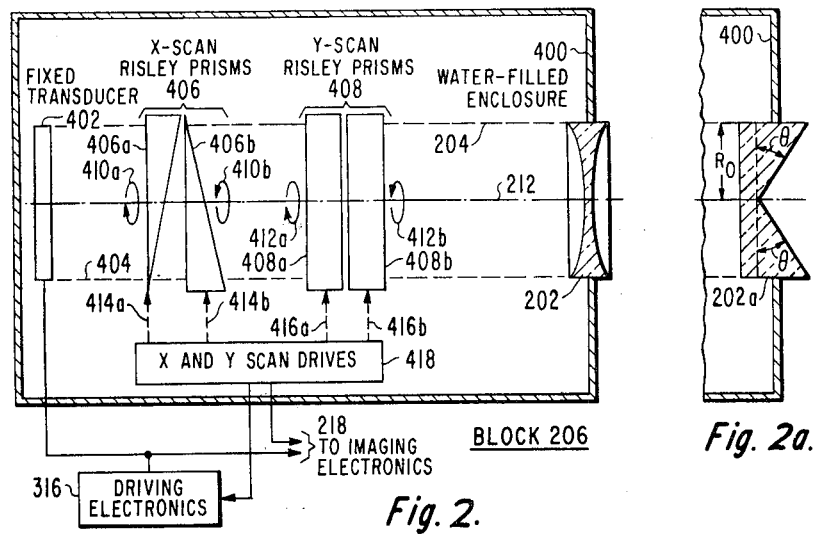
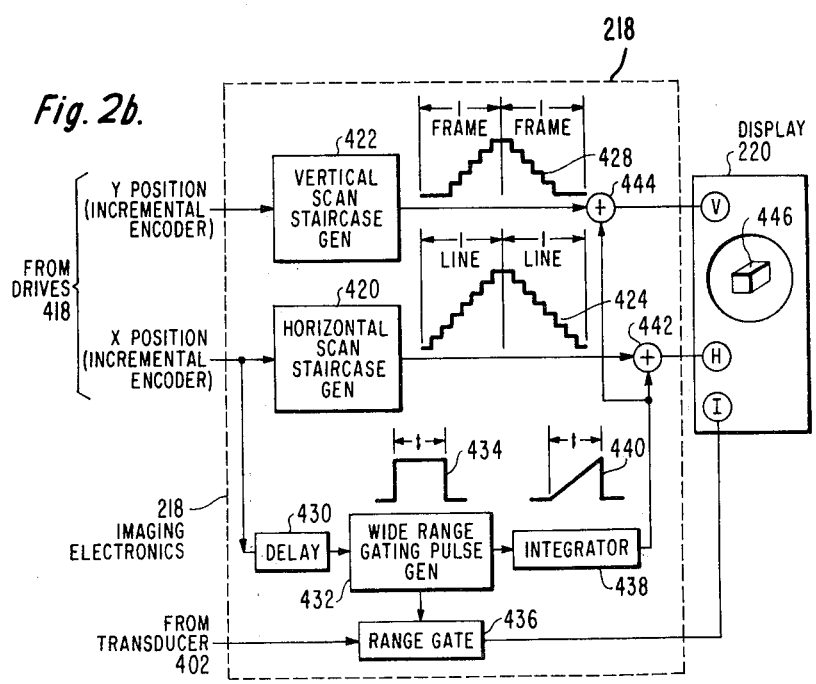

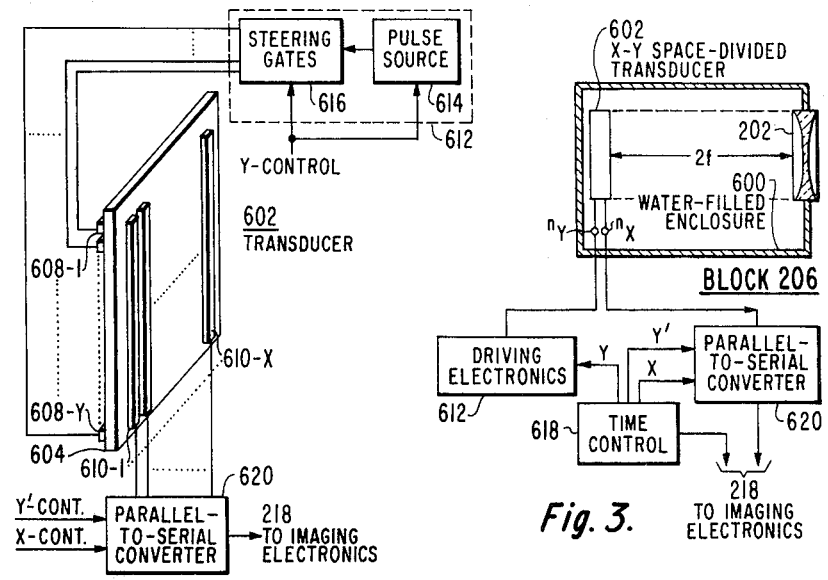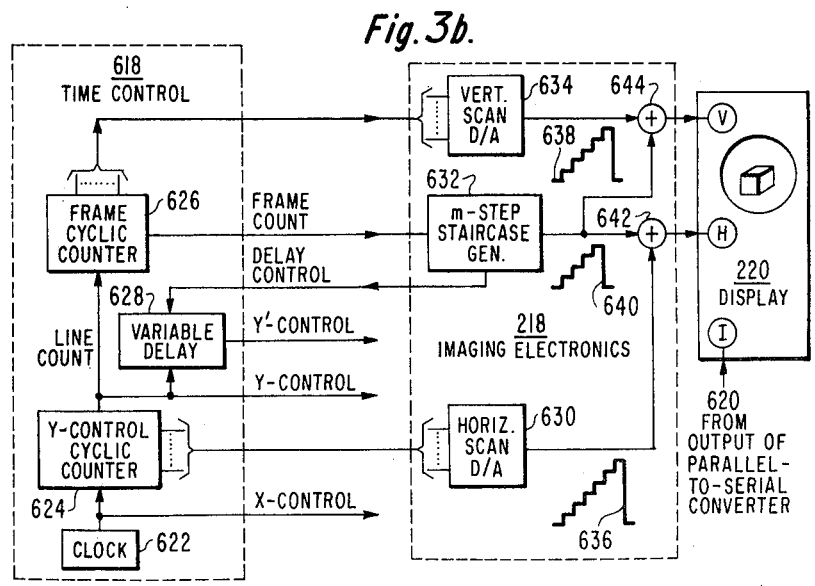

PULSE-ECHO ULTRASONIC-IMAGING DISPLAY SYSTEM

Reference should be made to the following U.S. patent applications, filed concurrently herewith and assigned to the same assignee as the present invention:

Ser. No. 766,564—Mezrich and Koenig
Ser. No. 766,565—Mezrich and Anderson
Ser. No. 766,528—Mezrich and Vilkomerson
Ser. No. 766,526—Mezrich and Avins The aforesaid U.S. patent application Ser. No. 766,564, Mezrich and Koenig, describes in detail a number of embodiments of a high resolution pulse-echo ultrasonic-imaging display system employing an acoustic focused device occupying a fixed aperture for both illuminating internal structure of a visually opaque object with a scanning focused beam of ultrasonic energy and for returning a reflected signal portion of the scanning focused beam passed therethrough for detection. The present application is directed to certain ones of these embodiments which are employed when the respective sizes of given parameters of the focusing device are related to the given wavelength of the ultrasonic wave energy to provide a given focused spot size for the scanning focused beam and also to provide depth of field for the scanning focused beam which is at least several times the given focused spot size.

In the drawings:

FIGS. 1 and 1a generically illustrate the type of pulse-echo ultrasonic-imaging system that may embody the present invention;

FIG. 2 illustrates a first species of the scanning ultrasonic source and detector of FIG. 1;

FIG. 2a shows a modification of the arrangement of FIG. 2, employing an axicon as the focusing device;

FIG. 2b shows a species of the imaging electronics of FIG. 1 that may be employed with the arrangement of FIG. 2 to provide an isometric display of a three-dimensional region of the internal structure being imaged;

FIGS. 3 and 3a illustrate a second species of the scanning of ultrasonic source and detector of FIG. 1, and FIG. 3b illustrates a species of the imaging electronics of FIG. 2 and a species of the time control of FIG. 3 which may be employed with the arrangement of FIG. 3 to provide an isometric display of a three-dimensional region of the internal structure being imaged.

FIGS. 1, 1a 2, 2a, 2b, 3, 3a and 3b of the present case correspond identically with respective FIGS. 2, 2a, 4, 4a, 4b, 6, 6a and 6b of the aforesaid U.S. patent application Ser. No. 766,564 (RCA 69,633).

Figure 1A:
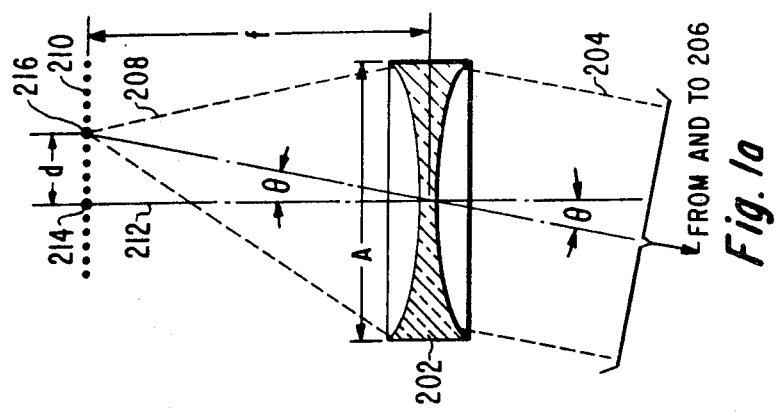
Figure 1:
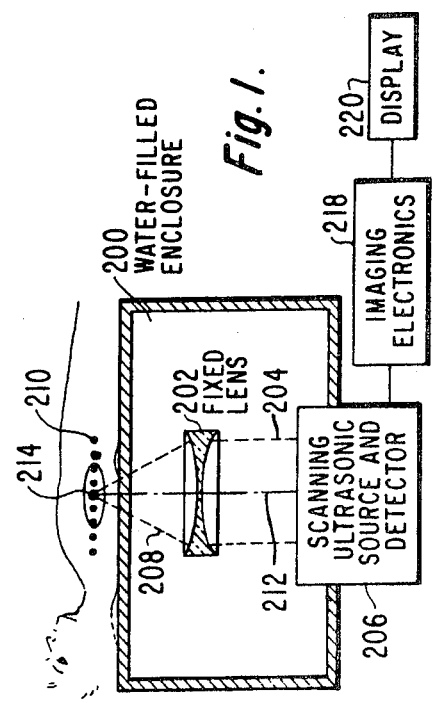

Referring to FIGS. 1 and 1a, there is shown a human patient lying on water-filled table 200. Immersed within water-filled table 200 is fixed lens 202, which is illuminated by a substantially plane wavefront beam 204 of ultrasonic energy from scanning ultrasonic source and detector 206 disposed in spaced relationship with fixed lens 202.

The term "fixed" lens, as used herein, means that the effective position of the aperture of lens 202 remains substantially stationary with respect to the human patient lying on water-filled table 200 during an image scan. However, in order to select the particular soft tissue within the human patient to be imaged, the operating distance between lens 202 and the human patient may be adjusted, if desired, prior to an image scan, by either changing the height of the top of water-filled table 200 with respect to lens 202 or by changing the position of lens 202 with respect to the top of the water-filled table 200 without departing from the above definition of "fixed" lens. Further, since the mere rotation of a circularly symmetrical lens about its own axis has no effect at all on the position of lens aperture or the way the lens acts on ultrasonic energy transferred therethrough, such mere rotation of the lens about its own axis is to be construed as to be within the above definition of the term "fixed" lens. Fixed lens 202 transfers the ultrasonic energy in plane wavefront beam 204 incident thereon into converging beam 208, which focuses at a small spot of focal plane 210 of lens 202 (located within the body of the human patient).

FIG. 1 shows plane-wavefront illuminating beam 204 of ultrasonic energy at a point in its scan where its direction of travel is parallel to acoustic axis 212 of fixed lens 202. In this case, ultrasonic energy converging beam 208 emerging from fixed lens 202 focuses at a spot centered at a focal point 214 in focal plane 210 of lens 202. However, as shown in FIG. 1a, when plane wavefront illuminating beam 204 is at a point in its scan where its direction of travel is angularly displaced by angle $\theta$ from acoustic axis 212 of lens 202, converging beam 208 emerging from lens 202 focuses at a spot centered at point 216 in focal plane 210 of lens 202. As shown in FIG. 1a, point 216 is linearly displaced by a distance d from focal point 214. As is known in the optical art, the relationship between the distance d and the angular displacement $\theta$ is given by the following equation:

$$d = f\theta, \qquad (1)$$

where f is the focal distance of lens 202, as shown in FIG. 1a, and the maximum value of $\theta$ is sufficiently small (as is the case) to be substantially equal in radians to tan $\theta$.

It will be noted from equation 1 that the value of d varies linearly with $\theta$. Further, as the value $\theta$ varies during a scan, the position of the point, such as point 216, to which beam 208 converges remains in focal plane 210. This ensures a substantially flat-field image (neglecting the effect of any lens abberations).

Various specific embodiments of scanning ultrasonic embodiments of scanning ultrasonic source and detector 208 are described below in detail. However, for present purposes, all that need be said is that scanning ultrasonic source and detector 208 includes therein, at the very least, (1) transducer means and driving electronics therefor for deriving exploratory pulses of ultrasonic frequency at a suitable repetition rate, as is known in the art, which exploratory pulses are projected from scanning ultrasonic source and detector as illuminating beam 204; (2) means for controlling, selecting and/or varying the angular orientation with which illuminating beam 204 is projected to thereby control, select and/or vary the angle $\theta$ with which illuminating beam 204 is incident on fixed lens 202, and (3) a detector coupled to or forming part of the transducer for receiving echoes of the exploratory pulses that have been "captured" by fixed lens 202 and received by the transducer of scanning ultrasonic source detector 206. In addition to these essential elements of scanning ultrasonic source and detector 206, block 206 may further include, when required or desired, such means as a collimating lens, a beam expander, a multi-element transducer with suitable controls for selecting a single or a subgroup of elements, an iris (which may be located in the vicinity of fixed lens 202) for adjusting the effective aperture of fixed lens 202 or any other means which may enhance the functional capability of scanning ultrasonic source and detector 206.

In any case, as is conventional, scanning ultrasonic source detector 206 derives an output signal manifesting detected echoes as a function of time along with suitable scan sync signals which are applied as an input to imaging electronics 218. Imaging electronics, which may be conventional, can include such means as range gates, scan converters, display deflection circuits synchronized with the scanning of illuminating beams 204, etc., to produce at the output thereof signals manifesting the relative intensity at each point of the image and one or more spatial coordinates of this point. As is conventional, this information is applied as the input to display 220, which may be a CRT display. In response thereto, the display derives a visual image of the "scene" within a region of the human patient scanned by converging ultrasonic beam 208.

The smallest detail of the visual image of the "scene" which can be resolved is even smaller than the size of the focused spot in focal plane 210 because fixed lens 202 also operates on the reflected echo returned to scanning ultrasonic source and detector 208, in addition to operating on the original illuminating beam therefrom. In quantitative terms, the diameter $\Delta$ of the focused spot and the smallest resolvable detail $\Delta'$ in the image respectively, are given by the following equations:

$$\Delta = 2.44 \, (f \lambda / A) \qquad (2)$$

and $$\Delta' = 1.46 \, f \lambda / A, \qquad (3)$$

where $\lambda$ is the wavelength of the propagating ultrasonic wave energy, and f and A are respectively the focal length and the aperture of fixed lens 202, shown in FIG. 1a.

Practical values for the aperture A and the focal length f of fixed lens 202, by way of example, are 5 inches and 10 inches respectively. If for example, the frequency of the ultrasonic energy is 3 MHz, the value of the propagation wavelength is substantially 0.5 mm. Substitution of these example values, in equation 3, indicates that a resolvable image spot diameter $\Delta'$ of 1.46 mm is obtained. By employing a fixed lens 202 having a larger value numerical aperture (i.e. a larger ratio of A/f) and/or employing ultrasonic energy at a frequency higher than 3 MHz, the image resolution capability can be increased even further. In general, depending upon the specific type of tissue being imaged and the depth of the tissue, optimum resolution in the range of 0.5–2.5 mm may be accomodated by a suitable choice of values for the parameters $\lambda$, f and A of equations 2 and 3.

As is known in optics, the depth of field $\delta$ is given by the following equation:

$$\delta = 4\lambda \, (f/A)^2 \qquad (4)$$

It can be seen from equation 4 that the depth of field $\delta$ varies inversely with the square of the value of the numerical aperture. In optics, this relationship cannot be practically exploited because the very small wavelength of light (i.e. 0.4–0.7 $\mu$m) causes the depth of field for a high numerical aperture lens to become very small. However, in ultrasonics, where the value of the propagating wavelength $\lambda$ is in the range of 0.15–1.5 mm. (for frequencies of 1–10 MHz), a relatively large depth of field is retained even for a relatively large numerical aperture lens. For instance, in the practical example discussed above, where lens 202 has a focal length f of 10 inches and an aperture A of 5 inches, and the propagating wavelength $\lambda$ is 0.5 mm., equation 4 shows that the depth of field $\delta$ still has a relatively large value of 8 mm (a value more than five times the image spot diameter of 1.46 mm). Further, as can be seen by comparing equation 4 with equations 2 and 3, the depth of field varies inversely with the square of the numerical aperture, while the spot diameter varies inversely only linearly with the numerical aperture. Thus, if desired, the depth of field can be increased significantly, with only a relatively small price in resolution capability, by relatively small reduction in the value of the numerical aperture of lens 202.

In fact, by using such means as an iris to stop down the effective aperture of a large aperture lens, a large depth field, relatively low resolution preliminary image may be obtained for the purpose of ascertaining the exact location of a desired target area, so that a fine adjustment may then be made in the relative position of lens 202 with respect to the patient to ensure that the desired target area substantially coincides with the focal plane of lens 202. After this fine adjustment has been made, the iris may be opened fully to permit a high resolution image of the target area to be obtained.

Some portion of the ultrasonic energy of beam 208 passing through the patient is scattered toward and then reflected from points laterally displaced from the one, (such as point 216) at which scanning ultrasonic beam 208 is then focused. Receipt and detection of reflections of such scattered ultrasonic energy would give rise to spurious signals. However, the arrangement shown in FIGS. 1 and 1a is substantially immune to such spurious signals because any ultrasonic energy reflected from points spaced from spot 216 which are returned to lens 202, in passing through lens 202, derive a beam corresponding to beam 204 oriented at angles displaced from angle $\theta$, shown in FIG. 1a. Therefore, the ultrasonic energy returned to the scanning transducer of block 206, which is detected, is substantially limited to primary reflected ultrasonic energy within the depth of field of each successive focused point, such as point 216, in focal plane 210 during a scan of the target area.

Referring now to FIG. 2, there is shown a first embodiment of scanning ultrasonic source and detector 206, which employs a fixed transducer. Specifically in FIG. 2, block 206 comprises water-filled enclosure 400 having a front wall which includes lens 202. Situated within enclosure 400 is relatively large aperture fixed transducer 402, which may comprise a piezoelectric plate. Fixed transducer 402, in response to exploratory pulse signals applied thereto from driving electronics 316, generates non-scanning ultrasonic energy beam 404. Raster-scanned ultrasonic beam 204, which illuminates lens 202, is derived from non-scanning ultrasonic beam 404 by being serially passed through both a pair of x-scan Risley prisms 406 and a pair of y-scan Risley prisms 408.

As known in the art of optics, a pair of Risley prisms may be used to substantially linearly deflect a beam of wave energy passing therethrough. In particular, one of the prisms of each pair is rotated continuously at a predetermined rate in a clockwise direction while the other prism of each pair is simultaneously rotated at the same predetermined rate in the counter-clockwise direction. That is, in FIG. 2, x-scan prism 406a is rotated at a relatively high first predetermined rate and y-scan prism 408a is rotated at a relatively low second predetermined rate in clockwise directions, as indicated by arrows 410a and 412a. Simultaneously, x-scan prism 406b is rotated at the first predetermined rate and y-scan prism 408b is rotated at the second predetermined rate in counter-clockwise directions, as indicated by arrows 410b and 412b. This rotation of x-scan prisms 406 and y-scan prisms 408 is achieved by mechanical couplings 414a, 414b, 416a and 416b from x and y scan drives 418. Drives 418 also supply scan sync signals to imaging electronics 218 and exploratory pulse repetition sync signals to driving electronics 316.

In FIG. 2, the relative assumed position shown for y-scan prisms 408a and 408b, with respect to each other is the same as the assumed relative position shown for x-scan prisms 406a and 406b, with respect to each other. However, the absolute assumed position of x-scan prisms 406 is in the plane of the paper, while the absolute assumed position of y-scan prisms 408 is in a plane perpendicular to the paper. With prisms 406 and 408 oriented in the assumed positions shown in FIG. 2, (because the deflection of ultrasonic beam 404 caused by prisms 414a and 416a, respectively, is cancelled by the deflection of ultrasonic beam 404 caused by prisms 414b and 416b, respectively) no net deflection of ultrasonic beam 204 occurs. However, counter rotation of prisms 406a and 406b from the assumed position by one-quarter cycle (in the direction indicated by arrows 410a and 410b) brings the bases of prisms 406a and 406b into alignment (in a plane parallel to but above the paper) to provide maximum deflection of beam 204 in the x-direction (perpendicular to the paper). At the end of one-half cycle of counter rotation of prisms 406a and 406b (in the direction indicated by arrows 410a and 410b), prisms 406a and 406b again point in opposite directions but now the base of prism 406a is at the bottom of the paper and the base of prism 406b is at the top of the paper. Again, cancellation occurs, and there is no net deflection of ultrasonic energy beam 204. At the end of three-quarters of a cycle of counter rotation of prisms 406a and 406b (in the direction indicated by arrows 410a and 410b), the bases of prisms 406a and 406b are aligned in a plane parallel to but below the paper. This results in a maximum deflection of ultrasonic energy beam 204 in the x-direction. The y-scan prisms 408 operate in a similar fashion, but because of the initial 90° displacement of y-scan prisms 408 with respect to x-scan prisms 406, y-scan prisms 408 deflect ultrasonic beam 204 in the y and -y directions (parallel to the paper) during each cycle of revolution thereof. Thus, each complete revolution of a Risley prism pair results in a pair of linear scans first in a given direction and then in a direction opposite to the given direction.

If each scan of the target area includes 10,000 sample points (as assumed above), relatively high first predetermined rate for the x-scan of about 900 rpm for Risley prisms 406 and a relatively low rate for the y-scan of about 9 rpm for Risley prisms 408 results in a 3.3 second period raster scan of the target area by the focused beam of ultrasonic energy.

FIG. 2a shows a modification of the arrangement shown in FIG. 2, in whch an acoustic axicon is substituted for lens 202 as the focusing device of block 206. An optical axicon, which may take the form of a cone, described by J. H. McLeod, J.O.S.A. 44, p. 592 (1954), when illuminated with a plane wave oriented normal to the axis of the axicon, focuses the incident light along a certain line segment of the axis of the axicon (rather than to a focal point as does a lens). This has the advantage of providing a much greater depth of field than a lens. The only effect of angularly displacing the orientation of the incident plane waves with respect to the normal to the axis of the axicon is to produce an angular shift in the orientation of the focused line segment. Furthermore, for angular displacements of the incident wave at least as large a $\pm 10°$, this angular shift is substantially equal to the incident angular displacement.

In more quantitative terms, if (as shown in FIG. 2a) the radius of the axicon is $R_0$, the angle of the conically-shaped cut away portion of axicon 202a with respect to the normal to the axis thereof is $\theta$, while the normalized index of refraction of the axicon material with respect to that of the surrounding ambient (water) is n and the wavelength of the ultrasonic wave energy is $\lambda$, the range (length of the focused line segment) and beam spot size (diameter of the focused line segment are then $$\text{range} = \frac{R_0}{(1-n)\tan\theta} \quad (5)$$

$$\text{spot size} = \frac{.38\lambda}{(1-n)\tan\theta} \quad (6)$$

By way of example, if the axicon is composed of polystyrene (n.64), wavelength $\lambda$ is 1 mm the radius $R_0$ is about 60 mm. and the axicon angle $\theta$ is 26.5°, the beam spot size is substantially constant at 2 mm from the plane of the axicon out to about 400 mm.

Although the arrangement shown in FIG. 2a, with axicon 202a situated in the frontwall of water-filled enclosure 400, is to be preferred, axicon 202a could be placed between fixed transducer 402 and Risley prism 406 in the path of ultrasonic wave energy beam 404. In this latter case, the front wall of water-filled enclosure 400 would merely include a window for passing the focused line-segment ultrasonic wave energy.

When an acoustic axicon is employed as the focusing device, it is desirable that display 220 of FIG. 1 include both a B-scan CRT and a C-scan CRT. The B-scan, which may use no range gate or may use a relatively wide range gate, provides a display in the plane defined by the relatively fast scan (assumed to be in the x direction) and the axial range direction 212 (z-direction normal to the X-Y plane). Such a B-scan can be accomplished in real time (the approximately 33ms required for one-half revolution of the X-scan Risley prisms 406 in the assumed example). However, a C-scan using a narrow range gate to select the particular X-Y image plane cannot be achieved in real time (i.e. a C-scan in the assumed example takes about 3.3 seconds). Further, by changing the range interval time delay between the occurrence of an exploratory pulse and the generation of a narrow range gate,) the selected X-Y plane displayed as a C-scan may be changed.

Even when the focusing device takes the form of a lens, as in the arrangements of FIG. 2, the relatively large depth of field of the acoustic lens, set forth above in equation 4, makes it desirable to include both a B-scan CRT and a C-scan CRT in display 220. Alternatively, by employing the imaging electronics arrangement shown in FIG. 2b, it is possible to provide an isometric three-dimensional display on a single CRT of a selected target volume ultrasonically scanned by the arrangement of FIG. 2 or FIG. 2a.

More specifically, as shown in FIG. 2b, imaging electronics 218 may comprise horizontal scan staircase generator 420 and vertical scan staircase generator 422. An encoder incorporated in X and Y scan drives 418 applies each of a series of X position pulses as an input to horizontal scan staircase generator 420, each such position pulse corresponding to a predetermined angular increment of X-scan Risley prisms 406. In a similar manner, each of a series of Y position pulses corresponding to a predetermined angular increment of Y-scan Risley prisms 408 is applied as an input to vertical scan staircase generator 422. Horizontal scan staircase 420 may include a reversible counter and a digital-to-analog converter for producing as an output staircase wave 424 during each revolution of X-scan Risley prisms 406. In a similar manner, vertical scan staircase generator 422 produces as an output staircase wave 426 during each revolution of Y-scan Risley prisms 408.

The X position incremental encoders also are utilized in FIG. 2 to synchronize the repetition period of the exploratory pulses applied to transducer 402 by driving electronics 316. Therefore, the duration of each step of staircase wave 424 is equal to one repetition period of the exploratory pulses. Further, by generating each Y-position pulse from drive 418 at the end of each one-half cycle of X-scan Risley prisms 406, each step of staircase wave 428 corresponds in duration with a "one-line" period of staircase wave 424. Similarly, one-half cycle of Y-scan Risley prisms 408 corresponds in duration with one frame of the display.

Each X position pulse is also passed through delay 430, which provides a delay equal in duration to the time between the transmission of an exploratory pulse from transducer 402 and the receipt by transducer 402 of an echo returned from the closest portion of the internal structure volume to be displayed. The delayed position pulse triggers wide range gating pulse generator 432 to produce a rectangular pulse waveform 434 having a duration t corresponding to the depth of the internal structure volume to be displayed. Pulse 434 is used directly to open range gate 436, thereby permitting only the detected echoes returned from this depth to reach the intensity-control (z-axis) of display 220, as is conventional. However, in addition, gating pulse 434 is applied to integrator 438 to produce as an output ramp 440 during interval t of each range period. Therefore, the duration of ramp 440 may be only a small portion of each relatively short step of staircase waveform 424, as well as each relatively long step of staircase waveform 428. Summing operational amplifier 442 is used to add ramp 440 to staircase wave 424 and apply its output to the horizontal scanning input of display 220. In a similar manner, operational amplifier 444 is used to add ramp 440 to staircase wave 428 and apply its output to the vertical scanning input of display 220. As indicated by cube 446, the addition of ramp 440 to the horizontal and vertical scan results in a three-dimensional isometric format for the display of the intensity-modulated range information of the ultrasonically scanned volume of internal structure. This three-dimensional isometric displayed format is an aid in visualizing the internal structure of complex shapes, such as the various shapes of human tissue.

Referring now to FIGS. 3 and 3a, there is shown a space-divided embodiment of scanning ultrasonic source and detector 206 for providing real-time scanning of the target area. Lens 202 is incorporated into the front wall of water-filled enclosure 600. Immersed in water-filled enclosure 600 is X-Y space-divided transducer 602. Transducer 602 is preferably situated at a distance from lens 202 equal to twice its focal length (2f), as indicated in FIG. 3, so that points on transducer 602 are imaged with unity magnification on a target area plane situated at a distance beyond lens 202 also equal to 2f. Similarly, points in the target area will be imaged with unity magnification at transducer 602. As shown in FIG. 3a, transducer 602 comprises piezo-electric plate 604 having a first set of driving line-section electrodes 608-1 . . . 608-y on the left surface thereof and a second set of sensing line-section electrodes 610-1 . . . 610-x on the right face thereof. As shown, the second set of electrodes is orthogonally oriented with respect to the first set of electrodes to thereby define (x · y) cross points therebetween. Each of these cross points corresponds to a sampling point of the target area. If, as has been assumed, x and y both have a value of 100, the total number of sampling points in the scan of the target area is 10,000.

Driving electronics 612 for energizing transducer 602 comprises pulse source 614 and steering gate 616. More specifically, under the control of Y signals from time control 618, steering gate 616 operates as a commutator to selectively supply successive exploratory pulses in sequence to each of driving electrodes 608-1 . . . 608-y, while simultaneously grounding all the non-selected remaining ones of this first set of electrodes. At the time an exploratory pulse is applied to driving electrodes 608-1 . . . 608-y, sensing electrodes 610-1 . . . 610-x are also grounded. This results in a narrow (e.g. 1 mm.) line beam of ultrasonic energy consisting of the energy launched from each of the cross-points of the then-selected one of driving electrodes 608-1 . . . 608-y.

Because each sampling point of the target area is imaged at a corresponding cross-point of the transducer in the arrangement of block 206 shown in FIGS. 3 and 3a, the round-trip travel time between the transmission of an exploratory pulse and the receipt of an echo from the target area in response thereto is twice that of the previously-discussed embodiments of block 206. More specifically, if the target area is situated ten inches beyond lens 202 (i.e. 2f=10 inches) as has been assumed, the total distance between transducer 602 and the target area is 20 inches. Therefore, the round trip travel time is in the order of 660 $\mu$s (assuming a velocity of 1500 m/s for the ultrasonic energy in the propagating medium).

Y control signals are applied to pulse source 614 in steering gates 616 at the beginning of a Y repetition period equal to or slightly greater than the round-trip travel time (660 $\mu$s) to cause each respective driving electrode 608-1 . . . 608-y to launch an exploratory pulse of ultrasonic energy in consecutive order at substantially 660 $\mu$s intervals.

Parallel-to-serial converter 620, which includes a set of x storage elements, a set of input gates under the control of Y' signals from time control 618 for applying the signals sensed by the sensing electrodes 610-1 . . . 610-x to the corresponding storage elements at or near the end of each Y (660 $\mu$s) period, and a steer-out circuit under the control of X-signals from time control 618 for sequentially reading out all the stored signals on the set of storage elements during the following Y period to thereby apply a serial stream of x (e.g. 100) sample point signals to imaging electronics 218 during that Y period. Time control 618 also supplies scan signals to imaging electronics 218. Thus, the scan of the entire target area takes (y+1) Y periods or, in the assumed example, 66.66 ms. This is a real-time frame rate of 15 scans of the target area per second.

At the end of any Y period, while parallel-to-serial converter 620 is sampling the echoes returned from the target area in response to the exploratory pulse transmitted from a particular one of driving line-section electrodes at the beginning of that Y period, it may be desirable for steering gate 616 to momentarily disconnect electrodes 608-1 . . . 608-y (i.e. allow electrode 608-1 . . . 608-y to float), in order to reduce the effective shunting parasitic load impedance between sensing electrodes 610-1 . . . 610-x and ground. This shunting load impedance tends to reduce the effective sensitivity and raise the effective signal-to-noise ratio of the sensed signals forwarded by sensing electrodes 610-1 . . . 610-x to the storage elements of parallel-to-serial converter 620. In any event, all other things being equal, the greater the number x-y cross-points, the greater is the effect of the shunting load impedance.

Referring now to FIG. 3b, there is shown a specific embodiment of time control 618 and imaging electronics 218 which provides an isometric three-dimensional display on a single CRT of a selected target volume ultrasonically scanned by the arrangement of FIGS. 3 and 3a. As shown in FIG. 6b, time control 618 may include clock 622 for generating X-control signals at a repetition rate equal to that of the serial stream of x sample point signals from parallel-to-serial converter 620. If, as assumed, there are 100 sample points within each Y period of 660 μs, clock 622 operates at a repetition frequency of about 150 kHz. The output from clock 622 is applied as an input to Y-control cyclic counter 624, which recycles at the end of each Y period (i.e., 100 counts in the assumed example) to provide a line count output at 1.5kHz. This line count output, besides being applied as an input to frame cyclic counter 626 and variable delay means 628, corresponds to the Y-control output from time control 618. In addition, the accumulated count within a cycle of Y-control cyclic counter 624 is applied as an input to horizontal scan digital to analog converter 630 of imaging electronics 218.

Frame cyclic counter 626 recycles after each frame (i.e., 100 lines in the assumed example) to apply a frame count input into m-step staircase generator 632 of imaging electronics 218. In addition, frame cyclic counter 626 applies a signal representative of the accumulated line count within a cycle as an input to vertical scan digital to analog converter 634 of imaging electronics 218.

The output from horizontal scan D/A is staircase wave 636, in which the duration of each step is equal to one clock period and the duration of the entire wave is equal to that of a line. Vertical scan D/A produces as an output staircase wave 638, in which the duration of each step is equal to that of a line and the duration of the entire wave is equal to that of a frame.

The m-step staircase generator 632 comprises a cyclic counter which recycles every m frame counts, analog or digital means responsive to the accumulated count in a cycle of this counter for applying a delay control signal to variable delay means 628 and a digital-to-analog converter for deriving staircase wave 640 in accordance with the accumulated count registered in the counter. Staircase wave 640 consists of m steps each having a duration equal to a frame count.

Staircase wave 640 is added to horizontal staircase wave 636 in summing operational amplifier 642 and applied to the horizontal scanning input of display 220. Further, staircase wave 640 is added to vertical staircase waves 638 in summing amplifier 644 and applied to the vertical scanning input of display 220. The serial stream of x sample signals forming the outputs from parallel-to-serial converter 620 is applied to the intensity-control input of display 220.

During a frame corresponding to the lowest step of staircase wave 640, the delay control signal is such as to cause variable delay 628 to provide a minimum delay between the occurrence of each Y-control signal (corresponding to the transmission of an exploratory pulse) and the occurrence of a Y' control signal (which opens the gates controlling the storage of detected echo signals by parallel-to-serial converter 620). Thus, the stream of x sample signals applied to the intensity-control input of display 220 corresponds with the nearest image plane of the internal structure target volume being displayed. Further, this nearest image plane is displayed in a C-scan format determined by the plurality of horizontal staircase waves 636 and the single vertical staircase wave 638 which occur within the duration of this lowest step of staircase wave 640. The next frame, which occurs within the duration of the second step is displayed as a second C-scan which is positioned slightly to the right of and above the first C-scan. At the same time, the value of the delay control signal during the second step of staircase wave 640 results in echoes from a somewhat more distant image plane of the internal structure target volume being applied to the intensity-control input of display 220 by parallel-to-serial converter 620. This process, which is repeated for each of the m steps in staircase waveform 640, results in an isometric three-dimensional display of the internal structure target volume on display 220.

By way of example, if the difference in delay provided by variable delay means, 628 between each pair of adjacent steps corresponds with a distance of about 2 mm (which is close to the limit of depth resolution at the ultrasonic wavelengths employed) and the value of m is 25, a three-dimensional isometric display of about a two-inch depth internal structure target volume is achieved.

What is claimed is:

1. In apparatus for use in an ultrasonic pulse-echo system capable of displaying an image of certain internal structure of a visually opaque object being scanned with ultrasonic wave energy, said apparatus including an acoustic focusing device occupying a given aperture which aperture remains substantially fixed in position with respect to said object while said object is being scanned, and ultrasonic beam forming means including transducer means generating successive pulses of ultrasonic wave energy and beam scanning means for illuminating said certain internal structure through said focusing device with a scanning focused beam of said pulsed ultrasonic wave energy, said transducer means being situated remotely from both said focusing device and from said internal structure for receiving and detecting a signal portion of said focused beam reflected from said certain internal structure and returned through said focusing device to said transducer means after a time delay proportional to the distance between said remotely situated transducer means and internal structure; the improvement:

wherein said ultrasonic wave energy has a given wavelength λ and wherein the respective sizes of given parameters of said focusing device are related to said given wavelength λ to provide a given focused spot size for said scanning focused beam and to provide a depth of field for said scanning focused beam which is at least several times said given focused spot size.

2. The apparatus defined in claim 1, wherein said focusing device is an acoustic lens having a given aperture A and a given focal length f, and wherein the diameter of said given focused spot Δ, the dimension Δ' of the smallest resoluable detail of the displayed image and the depth of field δ are related to said given wavelength λ, said given aperture A and said given focal length f by the following equations.

$$\Delta = 2.44 \frac{f \cdot \lambda}{A}$$

$$\Delta' = 1.46 \frac{f \cdot \lambda}{A}$$

$$\delta = 4\lambda \left(\frac{f}{A}\right)^2$$

3. The apparatus defined in claim 1, wherein said focusing device is an acoustic axicon.

4. The apparatus defined in claim 3, wherein said acoustic axicon is composed of a block of material having a conically-shaped cut away portion, said material exhibiting a normalized index of refraction n with respect to its surroundings which is less than unity and said conically-shaped cut away portion making an angle θ with respect to the axis thereof and having a maximum radius of $R_0$, and wherein the diameter of said given focused spot and the range of said depth of field are related to said given wavelength λ, said index of refraction n, said angle θ and said radius $R_0$ by the following equations:

$$\text{range} = \frac{R_0}{(1 - n) \tan \theta}$$

$$\text{spot size} = \frac{.38\lambda}{(1 - n) \tan \theta}.$$

5. The apparatus defined in claim 1, wherein said certain internal structure occupies a given volume having given length, width and depth dimensions, said depth dimension being no greater then said depth of field for said scanning focused beam and wherein said apparatus includes imaging electronics and display means coupled to said beam forming means and responsive to said detected signal portion of said focused beam for displaying a three dimensional representation of said structure in accordance with the respective values of all said volume dimensions.

6. The apparatus defined in claim 5, wherein said beam scanning means effectively provides an X-Y raster scan format for said scanning focused beam and generates corresponding raster sync signals, and wherein said imaging electronics and display means includes a CRT display intensity modulated in accordance with said detected signal portion of said focused beam and CRT scan-control means coupled between said beam forming means and said CRT display for diverting an isometric display of said certain structure on said CRT display in accordance with the time of generation of each pulse of ultrasonic wave energy and said raster sync signals.

7. The apparatus defined in claim 6, wherein said CRT scan-control means includes first means for generating a ramp signal occurring at a time following the generation of each successive pulse of ultrasonic wave energy during which a signal portion of said focused beam is being received from said depth of said volume second means for deriving a first signal equal to the sum of a first component and a second component, said first component being an analog of the instantaneous position in the X direction of said scanning focused beam and said second component being proportional to said ramp signal, third means for deriving a second signal equal to the sum of a third component and a fourth component, said third component being an analog of the instantaneous position in the Y direction of said scanning beam and said fourth component being proportional to said ramp signal, fourth means for coupling said first signal to said CRT display to control the sweep of said display in said first direction which correspond to said X direction, and fifth means for coupling said second signal to said CRT display to control the sweep of said display in a direction which is orthogonal to said first direction and which corresponds to said Y direction.

8. The apparatus defined in claim 6, wherein said scanning means provides at least one series of m successive frames of said X-Y raster scan, m being a plural integer, and wherein said imaging electronics and display means includes a CRT display, first means including variable delay means coupled to said CRT display for providing a displaced C-scan of the portion of said certain structure occupying a different selected length-width plane of said volume during each one of said successive frames, said displacement of said C-scan being along a given line oriented with respect to the C-scan sweep direction the amount of said displacement and the depth dimension of said sealed length-width plane being a substantially linear function of the amount of delay provided by said variable delay means, and second means for determining said amount of delay provided by said variable delay means in accordance with the ordinal value of each of said m frames in said series.

9. The apparatus defined in claim 8, wherein said second means changes said amount of delay in substantially equal distance increments between successive ones.

10. The apparatus defined in claim 9, wherein the smallest resolvable detail of the displayed image has a given size, and wherein each of said equal delay increments corresponds to a depth dimension increment no greater than said given size.

11. In apparatus for use in an ultrasonic pulse-echo system capable of displaying an image of certain internal structure of a visually opaque object being scanned with ultrasonic wave energy, said apparatus including an acoustic focusing device occupying a given aperture which aperture remains substantially fixed in position with respect to said object while said object is being scanned, and ultrasonic beam forming means including transducer means generating successive pulses of ultrasonic wave energy and beam scanning means for illuminating said certain internal structure through sid focusing device with a scanning focused beam of said pulsed ultrasonic wave energy, said transducer means being situated remotely from both said focusing device and from said internal structure for receiving and detecting a signal portion of said focused beam reflected from said certain internal structure and returned through said focusing device to said transducer means after a time delay proortional to the distance between said remotely situated transducer means and internal structure, the improvement:

- wherein said transducer means is situated in a given region in which said object is imaged by said focusing device, and said transducer means includes a first set of Y spaced parallel electrodes and a second set of X spaced parallel electrodes oriented orthogonally to and crossing the electrodes of said first set, where X and Y are given integers, to thereby define X-Y respective image sampling cross points, and
- wherein said ultrasonic beam focusing means further comprises first means for successively energizing each electrode of said first set a certain time after the energization of the preceding electrode of said first set to cause all the cross points of any energized electrode to simultaneously generate ultrasonic wave energy and after said time delay to simultaneously receive and detect corresponding signal portions of said focused beam, said certain time being at least equal to said time delay, respective sample storage means selectively coupled in parallel to respective ones of said second set of electrodes when signal portions of said focused beam corresponding to the respective sampling cross points of each electrode of said first set are being received and detected, said respective sample storage means separately storing each image sample of the individual electrode of said first set then being coupled thereto, and second means for serially reading out all said respective stored image samples in a time period immediately following the storing thereof, said time period being no greater than said certain time.

* * * * *

UNITED STATES PATENT AND TRADEMARK OFFICE
CERTIFICATE OF CORRECTION

PATENT NO. : 4,131,022
DATED : December 26, 1978
INVENTOR(S) : Reuben Saul Mezrich It is certified that error appears in the above-identified patent and that said Letters Patent is hereby corrected as shown below:

Column 1, line 53, delete (RCA 69,633)
Column 3, equation 2, delete ( )
Column 11, line 67, "diverting" should read --deriving--
Column 12, line 37, insert after "line oriented", --obliquely--
Column 12, line 39, "sealed" should read --selected--
Column 12, line 48, "distance" should read --discrete--
Column 12, line 65, "sid" should read --said--
Column 13, line 5, "proortional" should read --proportional--

Signed and Sealed this

Twenty-fourth Day of April 1979

[SEAL]

Attest:

RUTH C. MASON
Attesting Officer

DONALD W. BANNER
Commissioner of Patents and Trademarks